United States Patent [19]

Hostalek et al.

[11] Patent Number: 5,015,747

[45] Date of Patent: May 14, 1991

[54] ORGANOMETALLIC COMPOUNDS

[75] Inventors: Martin Hostalek; Ludwig Pohl, both of Darmstadt; Dietrich Erdmann, Mühltal; Herbert Schumann; Uwe Hartmann, both of Berlin; Meino Heyen; Holger Jürgensen, both of Aachen, all of Fed. Rep. of Germany

[73] Assignee: Merck Patent Gesellschaft mit Beschränker Haftung, Darmstadt, Fed. Rep. of Germany

[21] Appl. No.: 348,624

[22] PCT Filed: Jul. 26, 1988

[86] PCT No.: PCT/EP88/00674

§ 371 Date: Apr. 7, 1989

§ 102(e) Date: Apr. 7, 1989

[87] PCT Pub. No.: WO89/01479

PCT Pub. Date: Feb. 23, 1989

[30] Foreign Application Priority Data

Aug. 8, 1987 [DE] Fed. Rep. of Germany ....... 3726485

[51] Int. Cl.$^5$ ............... C07F 5/00; C07F 5/06; C23C 16/18; C23C 16/20

[52] U.S. Cl. ............... 556/1; 556/13; 556/14; 556/20; 556/21; 556/22; 556/27; 556/30; 556/64; 556/68; 556/70; 556/170; 556/174; 427/58; 437/81

[58] Field of Search ............ 556/1, 13, 14, 20, 21, 556/22, 27, 30, 64, 68, 70, 170, 174; 427/58, 96, 248.1; 437/81, 250

[56] References Cited

U.S. PATENT DOCUMENTS

| 4,349,483 | 9/1982 | Beach et al. | 556/170 X |
| 4,816,594 | 3/1989 | Wengong et al. | 556/174 X |

FOREIGN PATENT DOCUMENTS

| 0108469 | 5/1984 | European Pat. Off. |
| 0260534 | 3/1988 | European Pat. Off. |
| 2123422 | 2/1984 | United Kingdom |
| WO85/04405 | 10/1985 | World Int. Prop. O. |

OTHER PUBLICATIONS

Chem. Abstracts, vol. 54, No. 24346i, (1960).

*Primary Examiner*—Arthur C. Prescott
*Attorney, Agent, or Firm*—Millen, White, & Zelano

[57] ABSTRACT

The invention relates to organometallic compounds which are stabilized intramolecularly and have a cyclic or bicyclic structure and to the use thereof for the preparation of thin films and epitaxial layers by gas phase deposition.

6 Claims, No Drawings

ORGANOMETALLIC COMPOUNDS

The invention relates to organometallic compounds containing aluminum, gallium or indium as the metals and having a cyclic or bicyclic structure and also to the use of these compounds for preparing thin films or epitaxial layers by gas phase deposition.

The deposition of these layers either from pure elements of group III or from combinations with other elements such as, for example, gallium arsenide, indium phosphide or gallium phosphide can be used for the production of electronic and optoelectronic switching components, compound semiconductors and lasers. The deposition of these layers is carried out from the gas phase.

The properties of these films are dependent on the deposition conditions and the chemical composition of the resulting film.

Suitable gas phase deposition methods are all known methods such as Metallo-Organic Chemical Vapor Deposition (MOCVD), Photo Metallo-Organic Vapor Phase (Photo-MOVP) in which the substances are decomposed by irradiation with UV light, Laser Chemical Vapor Deposition (Laser CVD) or Metallo-Organic Magnetron Sputtering (MOMS). The advantages compared with other methods are controllable layer growth, precise doping control and, due to the atmospheric or reduced pressure conditions, easy handling and uncomplicated production.

The MOCVD method uses organometallic compounds which decompose at a temperature below 1100° C. with deposition of the metal. Typical apparatuses which are currently used for MOCVD consist of a bubbler containing an inlet for the organometallic component, a reaction chamber containing the substrate to be coated and also a carrier gas source which should be inert towards the organometallic component. The bubbler is kept at a constant, relatively low temperature which is preferably above the melting point of the organometallic compound, but far below the decomposition temperature. Preferably, the reaction or decomposition chamber has a very much higher temperature which is below 1100° C. and at which the organometallic compound decomposes completely and the metal is deposited. By means of the carrier gas, the organometallic compound is evaporated and channeled into the decomposition chamber together with the carrier gas. The mass flow of the vapor can be readily regulated and thus allows controlled growth of the thin layers.

Up to now, gas phase deposition was carried out in most cases by using metal alkyls such as, for example, trimethylgallium, trimethylaluminum or trimethylindium. However, these compounds are extremely air-sensitive, self-igniting and some of them decompose even at room temperature. Therefore, complicated safety precautions are required for the preparation, transport, storage and use of these compounds. A few somewhat more stable adducts of metal alkyls with Lewis bases such as, for example, trimethylamine and triphenylphosphine are also known (for example as described in GB 2,123,422, EP-A 108,469 or EP-A 176,537), but those are only of limited use for gas phase deposition due to their low vapor pressures.

The object of the present invention was therefore to find metal alkyl compounds which are easily handled and are stable at room temperature and which can be decomposed from the gas phase, that is metal alkyl compounds which are suitable for the different methods of gas phase deposition.

It has now been found that the intramolecularly stabilized compounds of aluminum, indium and gallium which have a cyclic or bicyclic structure are distinguished by a high resistance to air and oxygen and therefore are easily handled and highly suitable for gas phase deposition.

The invention therefore provides organometallic compounds of the formula I

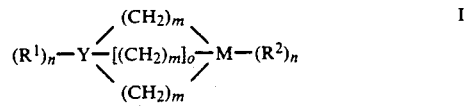

in which
$R^1$ and $R^2$ independently of one another are each H, a straight-chain or branched alkyl group having up to 7 C atoms, which can be partially or completely fluorinated, a cycloalkyl, alkenyl or cycloalkenyl group having each 3–8 C atoms or an unsubstituted or substituted phenyl group,
M is Al, In or Ga,
Y is N, P, As or Sb,
m is 2, 3 or 4,
n and o are each 0 or 1 and
n+o is 1.

The invention further provides the use of compounds of the formula I for gas deposition and also a process for the preparation of thin films or epitaxial layers by gas phase deposition of the metal from organometallic compounds where the organometallic substances are compounds of the formula I.

The compounds of the formula I have a cyclic or bicylcic structure and are intramolecularly stabilized by electron transfer from the inner nitrogen, phosphorus, arsenic or antimony atom to the electron-deficient IIIB element. Compared to the free metal alkyls used up to now, they therefore have a high resistance to air and oxygen. They are no longer self-igniting and therefore easy to handle. Yet, these compounds can be easily decomposed in the gas phase with deposition of the metals.

In formula I M is gallium, aluminum or indium. Preferably, M is gallium or aluminum. Y is preferably nitrogen, phosphorus or arsenic, nitrogen is particularly preferred.

m in the $(CH_2)_m$ groups independently of one another can be 2, 3 or 4. Preferably, m is 2 or 3 and preferably m in the $(CH_2)_m$ groups has the same meaning.

n and o can be each 0 or 1, where n+o=1. Preferably, n+1 and o=0.

The radicals $R^1$ and/or $R^2$ in formula I can be each a straight-chain or branched alkyl group having up to 7 C atoms, preferably 1–4C atoms. Accordingly, they are preferably methyl, ethyl, propyl, butyl, isopropyl, sec.-butyl, tert.-butyl, but also pentyl, hexyl, heptyl, 2-methylpentyl, 3-methylpentyl or 2-heptyl. The alkyl radicals can be partly or even completely fluorinated and can be, for example, monofluoromethyl, trifluoromethyl, difluoroethyl, trifluoroethyl, pentafluoroethyl or trifluoropropyl.

If $R^1$ and/or $R^2$ are a cycloalkyl or cycloalkenyl group, they are preferably cyclopentyl, cyclohexyl or cyclohexenyl. $R^1$ and $R^2$ can also be alkenyl groups having 3–8 C atoms, that is, for example, propenyl, butenyl, pentenyl, hexenyl, heptenyl or allyl. If $R^1$ and/or $R^2$ are a phenyl group, this phenyl group is preferably unsubstituted, but it can also be substituted. Since these substituents do not have a significant effect on the desired practical use, all substituents which do not interfere in the decomposition reaction are acceptable.

The following compounds represent a smaller group of preferred compounds of the formula I:
1,5-dimethyl-1-galla-5-aza-cyclooctane
1,5-diethyl-1-galla-5-aza-cyclooctane
1,5-dipropyl-1-galla-5-aza-cyclooctane
1,5-dimethyl-1-alumina-5-aza-cyclooctane
1,5-diethyl-1-alumina-5-aza-cyclooctane
1,5-diisopropyl-1-alumina-5-aza-cyclooctane
1,5-dibutyl-1-alumina-5-aza-cyclooctane
1-methyl-5-ethyl-1-galla-5-aza-cyclooctane
1-ethyl-5-methyl-1-alumina-5-aza-cyclooctane
1-cyclohexyl-5-methyl-1-galla-5-aza-cyclooctane
1,6-dimethyl-1-galla-6-aza-cyclodecane
1,6-dimethyl-1-alumina-6-aza-cyclodecane
1,6-diethyl-1-galla-6-aza-cyclodecane
1-phenyl-5-methyl-1-galla-5-aza-cyclooctane
1,4-dimethyl-1-galla-4-aza-cyclohexane
1,6-diethyl-1-alumina-6-aza-cyclodecane
1-galla-5-aza-bicyclo[3.3.3]undecane
1-galla-4-aza-bicyclo[2.2.2]octane
1-alumina-5-aza-bicyclo[3.3.3]undecane
1-alumina-4-aza-bicyclo[2.2.2]octane
1-methyl-5-cyclohexyl-1-galla-5-aza-cyclooctane
1-methyl-5-phenyl-1-galla-5-aza-cyclooctane
1-ethyl-5-phenyl-1-alumina-5-aza-cyclooctane
1-galla-6-aza-bicyclo[4.4.4] tetradecane
1-alumina-6-aza-bicyclo[4.4.4] tetradecane
1,5-dimethyl-1-inda-5-aza-cyclooctane
1,5-diethyl-1-inda-5-aza-cyclooctane
1,5-dipropyl-1-inda-5-aza-cyclooctane
1,5-diisopropyl-1-inda-5-aza-cyclooctane
1,5-dibutyl-1-inda-5-aza-cyclooctane
1-methyl-5-ethyl-1-inda-5-aza-cyclooctane
1-ethyl-5-propyl-1-inda-5-aza-cyclooctane
1-cyclohexyl-5-methyl-1-inda-5-aza-cyclooctane
1,6-dimethyl-1-inda-6-aza-cyclodecane
1,6-diethyl-1-inda-6-aza-cyclodecane
1-phenyl-5-methyl-1-inda-5-aza-cyclooctane
1,4-dimethyl-1-inda-4-aza-cyclohexane
1-inda-5-aza-bicyclo[3.3.3]undecane
1-inda-4-aza-bicyclo[2.2.2]octane
1-methyl-5-cyclohexyl-1-inda-5-aza-cyclooctane
1-methyl-5-phenyl-1-inda-5-aza-cyclooctane
1-inda-6-aza-bicyclo[4.4.4]tetradecane.

The compounds of the formula I are highly suitable for MOCVD epitaxy or the MOCVD method because they decompose at elevated temperatures with liberation of the corresponding metal. They are also suitable for the other methods of gas phase deposition such as Photo-MOVP, Laser CVD or MOMS.

The compounds of the formula I are prepared by methods which are known per se and as described in the literature (for example G. Bäahr, P. Burba, Methoden der Organischen Chemie (Methods of Organic Chemistry), volume XIII/4, Georg Thieme Verlag, Stuttgart (1970)), using reaction conditions which are known and suitable for the reactions mentioned. Variations which are known per se but not mentioned here can also be used.

Thus, compounds of the formula I can be prepared, for example, by reacting metal alkyl chlorides with an alkali organometallic compound of the corresponding Lewis base or a Grignard compound in an inert solvent.

Preferably, the reactions are carried out in inert solvents. Suitable solvents are those which do not interfere in the reaction and do not participate in the reaction process such as, for example, diethyl ether or tetrahydrofuran. The reaction temperatures are essentially those which are known from the literature for the preparation of similar compounds.

In the process according to the invention for the preparation of thin films or epitaxial layers on any desired substrate, the starting materials used in the gas phase deposition processes, known per se, of organometallic compounds are the intramolecularly stabilized organometallic compounds of the formula I.

To prepare compound semiconductors by the process according to the invention, one or more compounds of arsenic, antimony or phosphorus which are gaseous under the reaction conditions used, for example $AsH_3$, $AsMe_3$, $PH_3$ or $SbH_3$, are added to the decomposition chamber during the deposition process.

A further variation of the process according to the invention consists in adding doping substances in addition to the organometallic compounds according to the invention of the formula I during the deposition process. Doping substances which can be used are volatile organometallic compounds such as, for example, volatile organometallic compounds of iron, magnesium, zinc or chromium. Preferred compounds are for example $Zn(CH_3)_2$, $Mg(CH_3)_2$ or $Fe(C_2H_5)_2$.

The layers prepared by the process according to the invention can be used for the production of electronic and optoelectronic switching components, compound semiconductors or lasers.

Since only about 1% of the free metal alkyls used can be deposited on the substrate as an epitaxial layer in the epitaxy installations currently in use, the disposal of the excess metal alkyls, which cannot be recovered due to their extreme sensitivity, represents a significant problem. In contrast, the compounds according to the invention of the formula I open up new possibilities for the risk-free disposal or recovery of the valuable IIIB compounds.

The examples which follow are intended to illustrate the invention in more detail. Temperature data are always given in degrees Celsius. m.p. denotes melting point and b.p. denotes boiling point.

A: Preparation of the organometallic compounds:

EXAMPLE 1

2.9 g (119 mmol) of magnesium granules are initially introduced into 100 ml of THF and heated to reflux. 10 g (54 mmol) of bis(3,3'-chloropropyl)methylamine dissolved in 40 ml of THF are added. The mixture is then refluxed for another 2 hours.

7.8 g (50 mmol) of methylgallium dichloride in 20 ml of THF are added to the Grignard solution at room temperature. The mixture is stirred at room temperature for 24 hours and then heated to reflux for 3 hours. The solution is decanted from precipitated $MgCl_2$ to give, after evaporation of the solvent, 1,5-dimethyl-1-galla-5-aza-cyclooctane by vacuum distillation as a white solid having an m.p. of 34° and a b.p. of 83°/12 torr.

The following compounds are prepared analogously:
1,5-diethyl-1-galla-5-aza-cyclooctane
1,5-dipropyl-1-galla-5-aza-cyclooctane
1,5-diisopropyl-1-galla-5-aza-cyclooctane
1,5-di-n-butyl-1-galla-5-aza-cyclooctane 1,5-diisobutyl-1-galla-5-aza-cyclooctane
1,5-di-tert.-butyl-1-galla-5-aza-cyclooctane
1,6-dimethyl-1-galla-6-aza-cyclodecane
1,6-diethyl-1-galla-6-aza-cyclodecane
1,6-dipropyl-1-galla-6-aza-cyclodecane
1,6-diisopropyl-1-galla-6-aza-cyclodecane
1,6-dibutyl-1-galla-6-aza-cyclodecane
1,6-di-tert.-butyl-1-galla-6-aza-cyclodecane
1,6-diisobutyl-1-galla-6-aza-cyclodecane
1,4-dimethyl-1-galla-4-aza-cyclohexane
1,4-diethyl-1-galla-4-aza-cyclohexane
1,4-dipropyl-1-galla-4-aza-cyclohexane
1,4-diisopropyl-1-galla-4-aza-cyclohexane
1,4-dibutyl-1-galla-4-aza-cyclohexane
1,4-diisobutyl-1-galla-4-aza-cyclohexane
1,4-di-tert.-butyl-1-galla-4-aza-cyclohexane
1-methyl-5-ethyl-1-galla-5-aza-cyclooctane
1-methyl-5-propyl-1-galla-5-aza-cyclooctane
1-propyl-5-methyl-1-galla-5-aza-cyclooctane
1-ethyl-5-methyl-1-galla-5-aza-cyclooctane
1-ethyl-6-propyl-1-galla-6-aza-cyclodecane
1-propyl-6-butyl-1-galla-6-aza-cyclodecane
1-methyl-6-ethyl-1-galla-6-aza-cyclodecane
1-methyl-4-ethyl-1-galla-4-aza-cyclohexane
1-propyl-4-methyl-1-galla-4-aza-cyclohexane
1-ethyl-4-butyl-1-galla-4-aza-cyclohexane

EXAMPLE 2

3.6g (148 mmol) of magnesium granules are introduced into 100 ml of THF and heated to reflux. 12 g (49 mmol) of 3-chloro-N,N-bis-(3-chloropropyl)-1-propanamine in 40 ml of THF are added and the mixture is heated for another 2 hours.

8.2 g (47 mmol) of gallium trichloride in 20 ml of THF are added to the Grignard solution at room temperature. The mixture is stirred at room temperature for 24 hours and then heated to reflux for 4 hours. This gives 1-galla-5-azabicyclo[3.3.3]undecane after removal of the solvent and purification by vacuum distillation.

The following compounds are prepared analogously:
1-galla-6-azabicyclo[4.4.4]tetradecane
1-galla-4-azabicyclo[2.2.2]octane.

B: Working example for the preparation of thin films

EXAMPLE 3

The bubbler is charged with 1,5-dimethyl-1-galla-5-azacyclooctane (prepared according to Example 1) and connected to the inert gas inlet and the decomposition chamber. Depending upon the partial vapor pressure of the reagent in the reactor, decomposition with gallium deposition occurs at temperatures of about 700°.

We claim:

1. An organometallic compound of the formula I

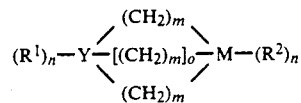

in which
R$^1$ and R$^2$ independently of one another are each H, a straight-chain or branched alkyl group having up to 7 C atoms, which can be partially or completely fluorinated, a cycloalkyl, alkenyl or cycloalkenyl group having each 3-8 C atoms or an unsubstituted or substituted phenyl group,
M is Al, In or Ga,
Y is N, P, As or Sb,
m is 2, 3 or 4,
n and o are each 0 or 1 and
n+o is 1.

2. The use of an organometallic compound of the formula I as claimed in claim 1 for the gas phase deposition of the metal on substrates.

3. The use of an organometallic compound of the formula I as claimed in claim 1 for the decomposition of epitaxial layers.

4. A process for the preparation of thin films on substrates by gas phase decomposition of the metal from organometallic compounds, wherein the organometallic compound used is a compound of the formula I

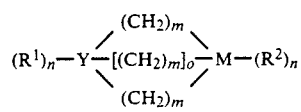

in which R$^1$, R$^2$, Y, M, m, n and o have the meanings given in claim 1.

5. The process as claimed in claim 4, wherein for the preparation of compound semiconductors one or more compounds of arsenic, antimony or phosphorus which are gaseous under the reaction conditions used are added during the deposition process.

6. The process as claimed in claim 4, wherein in addition to the organometallic compounds of the formula I doping substances are added during the deposition process.

* * * * *